United States Patent
Asahina et al.

[11] Patent Number: 5,942,518
[45] Date of Patent: Aug. 24, 1999

[54] WATER-SOLUBLE FLUOROETHYLCAMPTOTHECIN DERIVATIVE AND PROCESS FOR PRODUCTION THEREOF

[75] Inventors: Yoshikazu Asahina; Yasuo Oomori, both of Tochigi, Japan

[73] Assignee: Kyorin Pharmaceutical Co., Ltd., Tokyo, Japan

[21] Appl. No.: 08/952,366

[22] PCT Filed: Jun. 5, 1996

[86] PCT No.: PCT/JP96/01512

§ 371 Date: Nov. 18, 1997

§ 102(e) Date: Nov. 18, 1997

[87] PCT Pub. No.: WO96/41806

PCT Pub. Date: Dec. 27, 1996

[30] Foreign Application Priority Data

Jun. 8, 1995 [JP] Japan ................................. 7-141819

[51] Int. Cl.$^6$ .................... A61K 31/435; C07D 491/22
[52] U.S. Cl. .............................. 514/283; 546/48
[58] Field of Search ................ 546/48; 514/283

[56] References Cited

U.S. PATENT DOCUMENTS 4,943,579  7/1990  Vishnuvajjala et al. ................ 514/283

FOREIGN PATENT DOCUMENTS 471358  2/1992  European Pat. Off. .

OTHER PUBLICATIONS

Journal of Medicinal Chemistry, Sep. 1983, vol. 36, (Wall, et al) "Plant Antitumor Agents 30.Synthesis and Structure Activity of Novel Camptothecin Analogs" (pp. 2689–2700).

*Primary Examiner*—Evelyn Mei Huang
*Attorney, Agent, or Firm*—McAulay Nissen; Goldberg Kiel & Hand, LLP

[57] ABSTRACT

A compound represented by Chemical Formula (1), and salts thereof are provided.

A process for production thereof is also provided. The fluoroethylcamptothecin derivative has high antineoplastic activity, being less toxic, and water-soluble, thus is a useful compound.

27 Claims, No Drawings

WATER-SOLUBLE FLUOROETHYLCAMPTOTHECIN DERIVATIVE AND PROCESS FOR PRODUCTION THEREOF

This application is the national phase of PCT/JP96/01512, filed Jun. 5, 1996, published as WO 96/41806 on Dec. 27, 1996.

TECHNICAL FIELD

The present invention relates to a novel antitumor compound, and a process for producing the antineoplastic compound.

BACKGROUND TECHNIQUE

Camptothecin is an alkaloid isolated from Camptotheca acuminata (Wall, et al: J. Am. Chem. Soc., 88, 3888–3890 (1966)), and is known to exhibit antineoplastic activity by inhibiting nucleic acid synthesis (Lown, et al.: Biochem. Pharmacol., 29, 905–915, (1989)). However, as the results of the clinical tests in the United States, the development thereof as a medicine was discontinued because of its toxicity. Thereafter, derivatives of camptothecin are being studied to reduce the toxicity or to increase the activity, yet the problem of the high toxicity has not been solved. For example, irinotecan hydrochloride (Sawada, et al.: Chem. Pharm. Bull., 39, 1446–1454 (1991)), which is the most advanced antineoplastic medicine of camptothecin derivatives, involves problems of side effects of marrow inhibition as well as gastrointestinal toxicity which is considered to be caused by choline esterase inhibition resulting from the carbamoyl structure of the prodrug moiety introduced for making the compound water-soluble (Kawato, et al.: Kiso to Rinsho, 24, 229–234 (1990)).

As another example, 10,11-methylenedioxy-20-O-glycylcamptothecin, which has been reported recently as a water-soluble camptothecin derivative (Wall, et al: J. Med. Chem., 36, 2689 (1993)), has the structure analogous to the compound of the present invention, but has not yet been reported to have antineoplastic activity against solid tumor, and is highly toxic.

Furthermore, most of the camptothecin derivatives are hardly soluble in water, and is not suitable for intravenous administration as general clinical method, which is the great problem in development as a medicine. A fluoroethylcamptothecin derivative was disclosed (JP-A-5-17479) which is derived by changing the ethyl group on 20-position of a camptothecin derivative to a 2-fluoroethyl group having lower toxicity without impairing the antineoplastic activity. Such a compounds is also hardly soluble in water, and development thereof as the injectant is difficult.

DISCLOSURE OF THE INVENTION

Under such circumstances, comprehensive studies have been made by the inventors of the present invention to find a water-soluble fluoroethylcamptothecin derivative which has high antineoplastic activity and is less toxic than known camptothecin derivatives. Consequently, it was found that a glycidyl ester of 10-ethoxy-7-ethyl-18-fluorocamptothecin at hydroxyl group of 20-position has much more excellent antineoplastic activity and much higher safety than known camptothecin derivatives, and has water-solubility for use for intravenous administration. Based on the findings, the present invention has been completed.

The present invention provides a compound represented by Formula (1), and salts thereof:

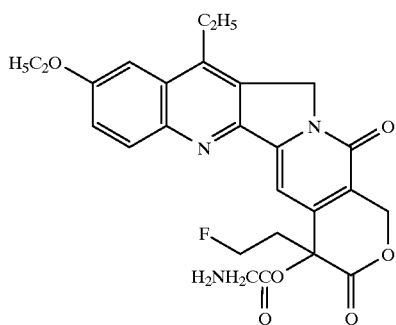

The compound of the present invention can be produced through the process exemplified by Reaction Formula 1 below.

More specifically, the compound represented by Formula (1) can be produced by reaction of Compound (2) with a glycine derivative having a protected nitrogen in a solvent such as a halogenated hydrocarbon like dichloromethane, and chloroform; an ether like tetrahydrofuran, dioxane, and ethylene glycol dimethyl ether; an aromatic hydrocarbon like benzene, and toluene; an amide like N,N-dimethylformamide, and N,N-dimethylacetamide; acetonitrile; or ethyl acetate, by use of a condensing agent, if necessary, such as N,N'-dicyclohexylcarbodimide, 1-ethyl-3-(3-dimethylpropyl)carbodiimide hydrochloride, and carbodiimidazole, in the presence of an amine such as triethylamine, diisopropylamine, pyridine, 4-(N,N-dimethylamino)pyridine, 1,8-diazabicylclo-7-undecene, and subsequent deprotection by action of an acid or a base, or by catalytic reduction. The reaction is conducted usually at −78° C. to 120° C., preferably from 0° C. to 120° C., for 10 minutes to 48 hours, preferably from 30 minutes to 24 hours.

The acid useful for salt formation is not specially limited provided that it is acceptable physiologically, and includes inorganic acids such as hydrochloric acid, sulfuric acid, and phosphoric acid; and organic acids such as formic acid, and acetic acid. The salt of the compound represented by Formula (1) can be produced directly by conducting the deprotection of the amino acid by use of the acid in a solvent such as water; an alcohol such as methanol, ethanol, and 2-propanol; an ether such as tetrahydrofuran, dioxane, ethylene glycol dimethyl ether; acetonitrile; or ethyl acetate. The reaction is usually conducted at −78° C. to 120° C., preferably from 0° C. to 120° C., for 10 minutes to 48 hours, preferably from 30 minutes to 24 hours.

Reaction Formula 1

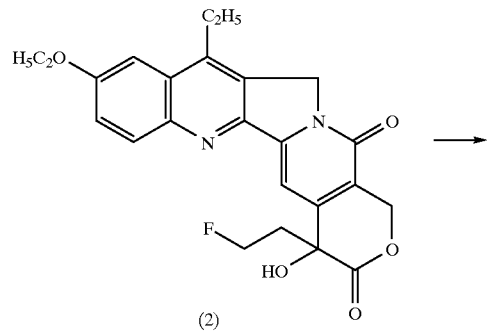

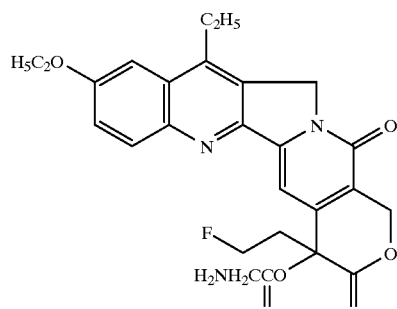

(1)

The effects of the present invention are described by reference to Experimental Examples.

Experimental Example 1

To ICR female mice of 5-week age, $5 \times 10^6$ cells of sarcoma 180 were implanted respectively under the skin of the axillary fossa. The medicine was administered to the tail vein three times from the day next to the administration at intervals of four days. After 14 days from the implantation, the tumors were enucleated and weighed. The antineoplastic effect is represented by the tumor growth inhibition rate (TGI=(1−T/C)×100) derived from the ratio (T/C) of the average tumor weight (T) of the medicine-administered group to the average tumor weight (C) of the control group. Table 1 shows the results.

Experimental Example 2

To CDF-1 female mice of 9-week age, $1 \times 10^6$ cells of mouse colonic cancer colon 26 were implanted respectively under the skin of the axillary fossa. The medicine was administered to the tail vein three times from six days after the administration when the tumor was detected by finger touch at intervals of four days. On the 17th to 19th days from the implantation, the tumors were enucleated and weighed. The antineoplastic effect is represented by the tumor growth inhibition rate (TGI=(1−T/C)×100) derived from the ratio (T/C) of the average tumor weight (T) of the medicine-administered group to the average tumor weight (C) of the control group. Table 2 shows the results.

Experimental Example 3

The inhibition of acetylcholine esterase reaction was measured by formation of thiocholine from acetylthiocholine iodide as the substrate by acetylcholine esterase and color reaction of the resulting thiocholine with dithiobisnitrobenzoic acid (DTNB) according to the method of Elleman, et al. (Biochem. Pharmacol., 7, 88–95, (1961). Specifically, to 2.6 mL of 0.1M sodium-phosphate buffer (pH=8.0), 0.1 mL of 10 mM DTNB solution, 0.1 mL of the enzyme solution or water, and 0.1 mL of the inhibitor solution. The mixture was kept at 25° C. for 15 minutes. Thereto, 0.1 mL of acetylthiocholine was added. The absorbance was measured at 412 nm. The reaction rate and the acetylthiocholine iodide concentration was plotted according to Lineweaver-Burk method to obtain $V_{max}$, and $K_m$. Then, the inhibition constant (Ki) was calculated from the inhibitor concentration. Table 3 shows the results.

TABLE 1

Effect against Mouse Sarcoma 180 Tumor

| Total dose (mg/kg) | TGI (%) | |
|---|---|---|
| | Example 1 | Irinotecan hydrochloride |
| 30 | — | 44 |
| 60 | 83 | 75 |
| 120 | 91 | 74 |

TABLE 2

Effect against Mouse Colonic Colon 26 Cancer

| Total dose (mg/kg) | TGI (%) | | |
|---|---|---|---|
| | Example 1 | Irinotecan hydrochloride | Compound 1* |
| 7.5 | — | — | 21 |
| 15 | — | — | 22 |
| 30 | 28 | 8 | 44 |
| 60 | 59 | 28 | (Toxic) |
| 120 | 81 | 34 (Toxic) | — |
| 180 | 82 | — | — |

*10,11-Methylenedioxy-20-O-glycylcamptothecin hydrochloride

TABLE 3

Comparison of Acetylcholine Esterase Inhibition

| | Ki value | Relative ratio |
|---|---|---|
| Irinotecan hydrochloride | 0.1–0.17 µM | 1 |
| Example 1 | 20–40 µM | 1/100 - 1/300 |

As shown in Table 1, the compound of the present invention, had higher inhibiting effect against the growth of sarcoma 180 tumor, an ordinary solid tumor, of mice in intravenous administration than irinotecan hydrochloride in the study of antineoplastic effects.

Further, as shown in Table 2, the compound of the present invention surprisingly had significant antineoplastic activity in intravenous administration against the growth of advanced colonic cancer 26 tumor of mice which is not inhibited by irinotecan hydrochloride, or 10,11-methylenedioxy-20-O-glycylcamptothecin hydrochloride having the structure analogous to the compound of the present invention. Thus the compound of the present invention has been proved to have antineoplastic activity higher than known camptothecin derivatives.

The compound of the present invention was nontoxic even at the total dose of 180 mg/kg, and was much safer not only than 10,11-methylenedioxy-20-O-glycylcamptothecin hydrochloride which is toxic at a dose of as low as 20 mg/kg but also than irinotecan hydrochloride.

As shown in Table 3, the compound of the present invention inhibited cholinesterase considerably less than irinotecan hydrochloride, being less liable to develop gastrointestinal disorder, such as, diarrhea. Further, the prodrug moiety, which is an amino acid, will not exhibit toxicity after the compound is converted in vivo to the mother compound.

Furthermore, the compound of the present invention has a water solubility necessary for the intravenous administration.

Thus the compound of the present invention is useful as an antineoplastic medicine because of the high antineoplastic activity, high safety, and water-solubility thereof.

The present invention is described below in more detail with Examples and Reference Example.

Best Modes for Practicing the Invention

EXAMPLE 1

Synthesis of 4-[(aminomethylcarbonyl)oxy]-9-ethoxy-11-ethyl-4-(2-fluoroethyl)-1H-pyrano[3',4':6,7]indolidino[1,2-b]quinoline-3,14(4H,12H)-dione hydrochloride 294 Milligrams of 9-ethoxy-11-ethyl-4-(2-fluoroethyl)-4-hydroxy-1H-pyrano[3',4':6,7]indolidino[1,2-b]quinoline-3,14(4H,12H)-dione, 235 mg of N-(t-butoxycarbonyl)glycine, 661 mg of 1-ethyl-3-(3-dimethylaminopropyl)carbodiimide hydrochloride, 50 mg of 4-(N,N-dimethylamino)pyridine, and 35 mL of methylene chloride were mixed. The mixture was stirred in an argon stream at room temperature for 1.5 hours. The reaction mixture was diluted with 30 ml of methylene chloride, washed with water, dried over anhydrous sodium sulfate, and concentrated. The resulting residue was purified by use of a silica gel column chromatography (elution solvent; methylene chloride:methanol=25:1). The eluted yellow foamed substance was dissolved in 3 mL of ethyl acetate saturated with hydrogen chloride (3 mol/L). The solution was stirred at room temperature for one hour. The deposited crystalline matter was collected by filtration. The collected crystalline matter was washed with ethyl acetate and subsequently with ether to obtain 290 mg of the intended yellow powdery matter.

Melting point: 201–210° C. (decomposed)

Elemental analysis, as $C_{26}H_{26}FN_3O_6 \cdot 2HCl \cdot 2H_2O$ Calculated (%): C, 51.66; H, 5.34, N, 6.95 Found (%): C, 51.57; H, 5.21; N, 7.20

EXAMPLE 2

Synthesis of (−)-4-[(aminomethylcarbonyl)oxy]-9-ethoxy-11-ethyl-4-(2-fluoroethyl)-1H-pyrano[3',4':6,7]indolidino[1,2-b]quinoline-3,14(4H,12H)-dione hydrochloride 10 Milligrams of (+)-9-ethoxy-11-ethyl-4-(2-fluoroethyl)-4-hydroxy-1H-pyrano[3',4':6,7]indolidino[1,2-b]quinoline-3,14(4H,12H)-dione, 8.0 mg of N-(t-butoxycarbonyl)glycine, 22.0 mg of 1-ethyl-3-(3-dimethylaminopropyl)carbodiimide hydrochloride, 2 mg of 4-(N,N-dimethylamino)pyridine, and 1 mL of methylene chloride were mixed. The mixture was stirred in an argon stream at room temperature for one hour. The reaction mixture was diluted with 2 mL of methylene chloride, washed with water, dried over anhydrous sodium sulfate, and concentrated. The resulting residue was purified by use of a silica gel column chromatography (elution solvent; methylene chloride:methanol=25:1). The eluted yellowish brown foamed substance was dissolved in 0.2 mL of ethyl acetate saturated with hydrogen chloride (3 mol/L). The solution was stirred at room temperature for 30 minutes. The deposited crystalline matter was collected by filtration. The collected crystalline matter was washed with ethyl acetate and subsequently with ether to obtain 3.6 mg of intended yellow solid substance.

Mass (FAB): m/e=496 [(M+H)$^+$]

$[\alpha]_D^{25}$=−67.2° C. (c=0.13, water)

Industrial Utility

The novel fluoroethylcamptothecin derivative of the present invention has high antineoplastic activity, being less toxic than conventional camptothecin derivatives, and water-soluble. Thus it is a useful compound.

We claim:

1. A compound represented by Formula (1) below, or a salt thereof:

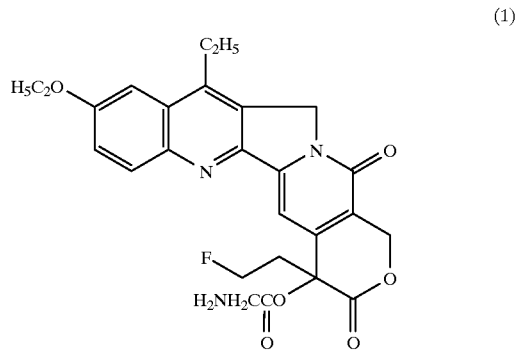

(1)

2. A process for producing the compound represented by Formula (1), or a salt thereof:

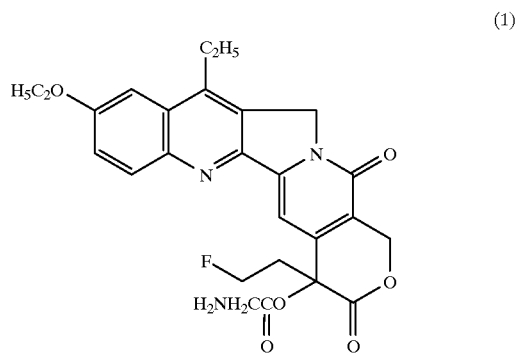

(1)

comprising reaction of a compound represented by Formula (2):

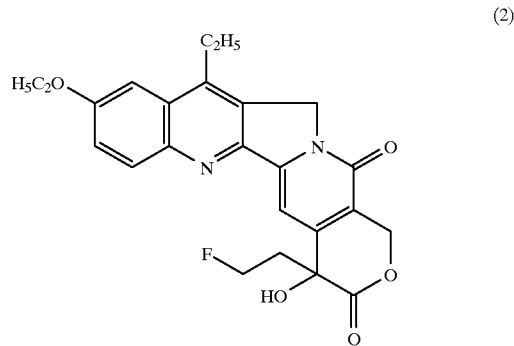

(2)

with a glycine derivative having a protected amino group, and subsequent deprotection.

3. The compound of claim 1, in the form of a physiologically acceptable salt formed from an acid selected from the group consisting of hydrochloric acid, sulfuric acid, phosphoric acid, formic acid and acetic acid.

4. The process of claim 2, wherein the reaction of the compound of Formula (2) with a glycine derivative occurs in a solvent selected from the group consisting of halogenated hydrocarbons, ethers, aromatic hydrocarbons, amides and ethyl acetate.

5. The process of claim 4, wherein the solvent is dichloromethane.

6. The process of claim 4, wherein the solvent is chloroform.

7. The process of claim 4, wherein the solvent is tetrahydrofuran.

8. The process of claim 4, wherein the solvent is dioxane.

9. The process of claim 4, wherein the solvent is ethylene glycol dimethyl ether.

10. The process of claim 4, wherein the solvent is benzene.

11. The process of claim 4, wherein the solvent is toluene.

12. The process of claim 4, wherein the solvent is N,N-dimethylformamide.

13. The process of claim 4, wherein the solvent is N,N-dimethylacetamide.

14. The process of claim 4, wherein the solvent is acetonitrile.

15. The process of claim 4, wherein the solvent is ethyl acetate.

16. The process of claim 2, wherein the reaction occurs in the presence of a condensing reagent.

17. The process of claim 16, wherein the condensing reagent is selected from the group consisting of N,N'-dicyclohexylcarbodiimide, 1-ethyl-3-(3-dimethylpropyl) carbodiimide hydrochloride, and carbodiimidazole.

18. The process of claim 2, wherein the reaction occurs in the presence of an amine.

19. The process of claim 18, wherein the amine is selected from a group consisting of triethylamine, diisopropylamine, pyridine, 4-(N,N-demethylamino)pyridine and 1,8-diazabicyclo-7-undecane.

20. The process of claim 2, wherein the deprotection occurs by action of an acid, a base or by catalytic reduction.

21. The process of claim 2, wherein the reaction is maintained between −78° C. and 120° C. for a period of from about 10 minutes to about 48 hours.

22. The process of claim 21, wherein the reaction is maintained between 0° C. and 120° C.

23. The process of claim 21, wherein the reaction is maintained from about 30 minutes to about 24 hours.

24. A method for inhibiting the growth of a tumor responsive to fluoroethylcamptothecin in a mammal comprising administering a tumor inhibiting effective amount of the compound of claim 1 to a mammal in need thereof.

25. The method of claim 24, wherein the administration is intravenous.

26. A composition comprising a compound of claim 1 and a pharmaceutically acceptable carrier.

27. A method for inhibiting the growth of a tumor responsive to fluoroethylcamptothecin in a mammal comprising administering a tumor inhibiting effective amount of the composition of claim 26 to a mammal in need thereof.

* * * * *